Figure 1:
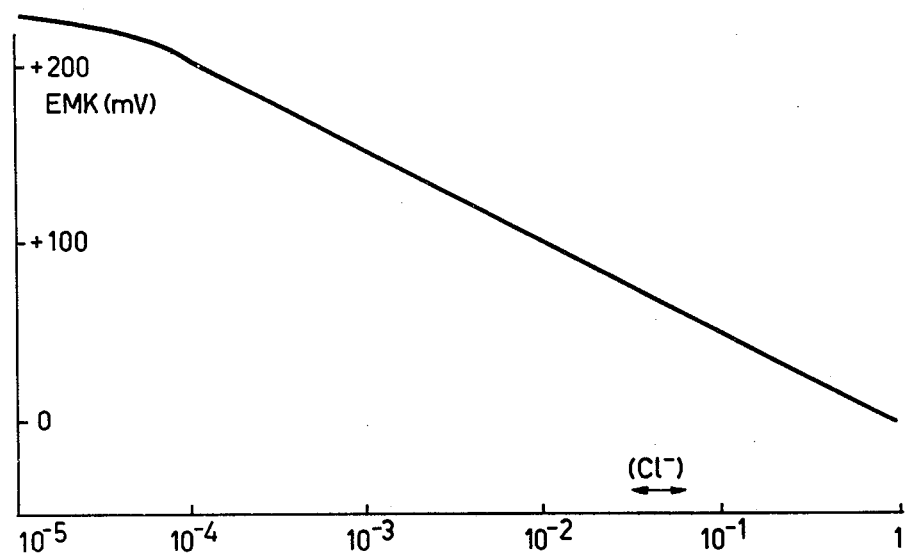

United States Patent [19]

Van de Leest et al.

[11] 4,083,764
[45] Apr. 11, 1978

[54] ION-SELECTIVE ELECTRODE

[75] Inventors: Renaat Edmond Van de Leest; Nicolaas Marinus Beekmans; Leopold Heijne, all of Eindhoven, Netherlands

[73] Assignee: U.S. Philips Corporation, New York, N.Y.

[21] Appl. No.: 640,704

[22] Filed: Dec. 15, 1975

[30] Foreign Application Priority Data

Jan. 24, 1975 Netherlands .................... 7500823

[51] Int. Cl.² ........................................ G01N 27/46
[52] U.S. Cl. ........................ 204/195 M; 427/126; 427/255; 427/430 R; 204/1 T; 204/56 R; 204/192 SP
[58] Field of Search ........... 204/195 M, 195 R, 195 G

[56] References Cited

U.S. PATENT DOCUMENTS

| 3,563,874 | 2/1971 | Ross et al. | 204/195 M |
| 3,649,506 | 3/1972 | Petersen et al. | 204/195 G |
| 3,657,093 | 4/1972 | Farren | 204/195 M |
| 3,723,589 | 3/1973 | Kennedy | 204/195 M |
| 3,822,198 | 7/1974 | Bauke | 204/195 M |
| 3,824,170 | 7/1974 | Weelink et al. | 204/195 M |
| 3,857,777 | 12/1974 | Guilbault et al. | 204/195 M |
| 3,892,833 | 7/1975 | Hattori et al. | 204/195 M |

Primary Examiner—T. Tung
Attorney, Agent, or Firm—Frank R. Trifari; Carl P. Steinhauser

[57] ABSTRACT

Ion-selective electrode for selectively measuring the concentration of an ion in a solution of a mixture of ions, consisting of an ion-conducting or mixed ion-conducting - electron-conducting matrix material provided with a thin surface coating of a material which is sparingly soluble and which has one ion in common with the matrix material.

2 Claims, 2 Drawing Figures

ION-SELECTIVE ELECTRODE

The invention relates to an ion-selective electrode and to methods of manufacturing such an electrode.

Such electrodes for selectively measuring concentrations of a certain ion in a mixture of different ions are known from United Kingdom Pat. specification No. 1,324,839, which electrode consists of at least two liquid-impermeable coatings of monocrystalline, polycrystalline, vitreous - crystalline or vitreous materials, which materials have a common ion.

There are also electrodes which consist of a mixture of two of such materials. (J. W. Ross and R. A. Durst: Ion-selective electrodes; chapter 2, NBS Special Publication 314 (1969)).

The object of this embodiment is to achieve sturdiness of the electrode, because many electrode materials in the form of thin coatings lack the required sturdiness for use as a self-supporting electrode. Therefore a material is used as a support which does have the required sturdiness. The proposed support materials such as AgCl and $Ag_2S$ have a high specific resistance. The electrodes equipped therewith were found to exhibit a rather slow response. The known electrodes are manufactured by placing a weighed quantity of material in a pulverulent form in a mould and by providing an evenly thick coating of the second material thereon after the first coating has been roughened in order to obtain a satisfactory contact. The assembly is subsequently compressed at a high pressure and, if necessary, at an elevated temperature. The poor reproducibility of the moulding operation results in products having divergent properties. This technique also results in a fairly moderate sensitivity of the electrodes.

The invention provides an ion-selective electrode having a large specific resistance, a large and reproducable sensitivity and a very fast response.

According to the invention the electrode is characterized in that it consists of an ion-conducting or mixed ion-conducting - electron-conducting matrix material having a specific ion conductivity of at least $2\times10^{-4}$ mho.$cm^{-1}$ on which at least one coating having a total thickness of 0.1–100$\mu$m is provided of a material having one ion in common with the adjacent material, while the coating which is in contact with the measuring medium has a solubility product of less than $10^{-9}$ at room temperature.

The matrix material may not only exhibit ion conductivity but also electron conductivity, but this is no drawback at all. One method of measuring the specific conductivity for ions is the one using direct voltage and using exclusively ion-conducting electrodes, for example, an electrode of AgI or a solution comprising the relevant ion.

The active material constituting the outer coating need not have a high ion conductivity; its optimum thickness depends on the specific ion conductivity; the lower this conductivity, the thinner the coating is preferably chosen.

This configuration provides many possibilities; as a matrix material mixed compounds such as iodide-sulphide, bromide-sulphide and iodide-pyrophosphate may be used. A novel possibility is an electrode capable of selectively measuring phosphate concentrations with silver phosphate as a reactive coating and a mixed pyrophosphate as a matrix material. Other possibilities for the matrix material are mixed compounds such as $xAg_2Se.yAg_3PO_4$, $xAg_2S.y Ag_{1.7}Te$. $AgPO_3$, $xAg_2S.yAg_{1.7}Te.zAg_4P_2O_7$ silver iodide-silver tungstate or $17CuI.3C_6H_{12}N_4.CH_3I$ and furthermore silver tetra-alkylammoniumiodide, $Ag_2HgI_4$, $Cu_2HgI_4$, or aluminates of the $\beta$-alumina type in which Na may be replaced by other metals or ammonium and Al may be replaced by Ga or In, which aluminate is superficially converted into bivalent aluminate.

A preferred method of manufacturing ion-selective electrodes according to the invention consists in that the ion-conducting matrix material is superficially converted chemically or electrochemically into the material which is sparingly soluble in the measuring medium and has one ion in common with the matrix material.

The said chemical reaction is a reaction at the phase boundary between the matrix material and a liquid or gaseous reagent. The coating thus provided need only be very thin (for example, 5$\mu$m). The active material therefore requires a less high specific ion conductivity than the matrix material. Since the latter is completely shielded, the selective response of the relevant ion is ensured. When the active coating has lost its activity, it can be removed and a completely new coating may be formed by the said conversion. Due to the slight thickness of the active coating and the low resistance of the matrix material, the response is very fast.

According to a further possible method of manufacturing the electrodes the active coating is provided on the matrix material by vapour deposition or by cathodic sputtering.

The following examples serve to illustrate the invention,

Firstly some chemical methods of preparing the active coating will be described.

Each time 1 g of pulverulent $Ag_3SI, Ag_3SBr, Ag_{19}I_{15}P_2O_7$ and $Ag_8I_4P_2O_7$ were molded with a diameter of 8mm with a silver contact. These materials were heated at temperatures of 150°, 150°, 100° and 85° C, respectively, and were contacted with gaseous $Cl_2, Br_2$ or $I_2$ for 1 hour, 1 hour, 5 min. and 5 min., respectively. The coatings obtained consisting of AgCl, AgBr or AgI had a thickness of 5$\mu$m at an average.

A similar pellet of $Ag_{19}I_{15}P_2O_7$ was allowed to react by maintaining it immersed for 12 hours in a concentrated Na-phosphate solution ($Na_3PO_4$). Such a pellet of $Ag_8I_4P_2O_7$ was sintered at 85° C and subsequently heated to the melting point. After cooling a vitreous pellet was obtained which was maintained immersed in a concentrated sodium phosphate solution after being etched in a 25% ammonium hydroxide solution and being exposed to daylight for 10 min.

Such a pellet of $Ag_3SBr$ was allowed to react with a concentrated solution of $CuCl_2$, producing the compounds AgCl, AgBr and $Cu_xS$, x being greater than 1. The silver halides were removed therefrom by concentrated ammonium hydroxide and the product was heated in sulphur vapour for defining the composition of CuS.

Some electrochemical examples of forming the active coating will now be described.

A pellet likewise molded as described above and comprising $Ag_3SBr, Ag_{19}I_{15}P_2O_7$ or $Ag_8I_4P_2O_7$ was held with a constant EMF against a platinum counter electrode in a solution of chloride-ions, bromide ions or iodide ions so that $Ag^+$- ions were generated which subsequently reacted with the said anions while forming an active coating. A further possibility is to form the coating under the passage of current with a current maintained constant.

The tables gives a survey of electrodes thus obtained.

| sub-strate | coating | preparation chemically | electro-chem. | measured ion |
|---|---|---|---|---|
| $Ag_3SI$ | AgCl | + | | Cl− |
| | AgBr | + | | Br− |
| | AgI | | | J− |
| $Ag_3SBr$ | AgCl | + | + | Cl− |
| | AgBr | | + | Br− |
| | AgI | | + | J− |
| $Ag_{19}I_{15}P_2O_7$ | AgCl | + | + | Cl− |
| | AgBr | + | + | Br− |
| | AgI | | + | J− |
| | $Ag_3PO_4$ | + | | $PO_4^{3-}$ $HPO_4^{2-}$ |
| $Ag_8I_4P_2O_7$ | AgCl | + | + | Cl− |
| | AgBr | + | + | Br− |
| | AgI | | + | J− |
| | $Ag_3PO_4$ | + | | $PO_4^{3-}$ $HPO_4^{2-}$ |
| $Ag_3SBr$ | $Cu_xS$ | + | | $Cu^{+-}$ |

Four different AgCl-electrodes consisting of an $Ag_3SI$-matrix with an AgCl-film manufactured as described above were used as electrodes for measuring Cl−-concentrations in the range of $10^{-5}$ to 1 gram ion/liter. FIG. 1 shows the sensitivity of the measurement: as from $10^{-4}$ gram ion/liter entirely in accordance with Nernst's law with an EMF slope of 58 mV/decade. The curves of the four electrodes coincide.

Figure 2:
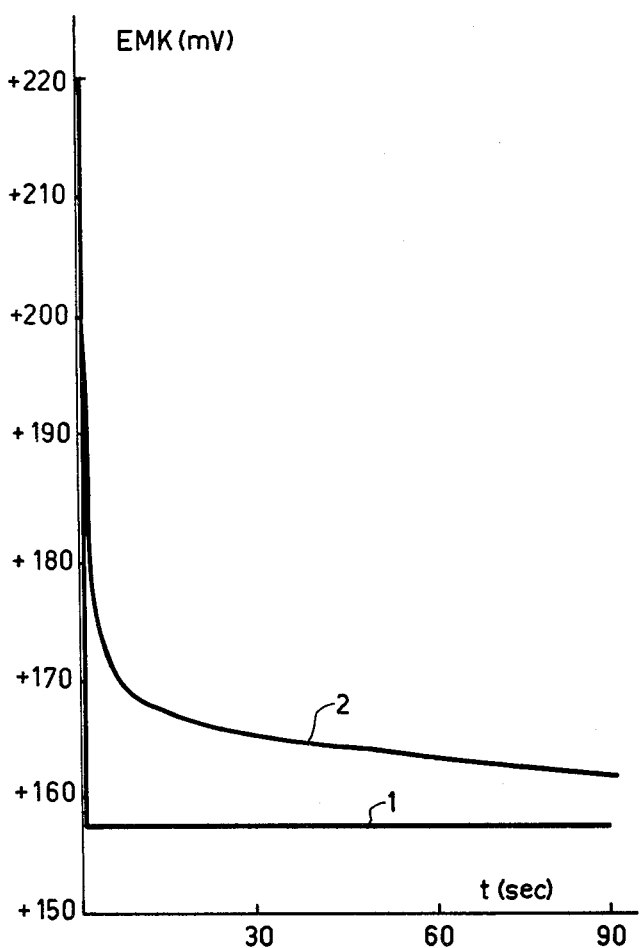

In FIG. 2 in which the EMF (in the drawing "EMK") in mV against a saturated calomel electrode is shown as a function of time, the response of an electrode according to the invention consisting of an $Ag_3SI$-matrix with an AgCl-film having a thickness of 5μm (1), obtained by causing the matrix to react with $Cl_2$-gas, is compared with a known electrode consisting of an $Ag_2S$-matrix around which a coating of AgCl is moulded (2), The curve (2) also applies to an embodiment in which a compressed mixture of $Ag_2S$ and AgCl is used.

Similar results are obtained with the other above-described electrodes for measurements on I−, Br−, $PO_4^{3-}$ and $HPO_4^{2-}$ and $Cu^{++}$.

What is claimed is:

1. An ion-selective electrode for selectively measuring the concentration of an ion in a solution of a mixture of ions, comprising an ion-conducting or a mixed ion-conducting - electron-conducting matrix material of a mixed silver-iodine pyrophosphate having a specific ion conductivity of at least $2 \times 10^{-4}$ mho.cm$^{-1}$, and at least one coating on said matrix having a thickness of between 0.1 and 100 um of an ion-selective material of a silver halide or silver phosphate.

2. An electrode as claimed in claim 1, wherein the coating is silver phosphate.

* * * * *